(12) United States Patent
Qiao et al.

(10) Patent No.: US 9,518,305 B2
(45) Date of Patent: *Dec. 13, 2016

(54) ORGANO-CATALYTIC BIOMASS DECONSTRUCTION

(71) Applicant: Virent, Inc., Madison, WI (US)

(72) Inventors: Ming Qiao, Pewaukee, WI (US); Randy D. Cortright, Madison, WI (US); Elizabeth Woods, Middleton, WI (US)

(73) Assignee: Virent, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/968,361

(22) Filed: Dec. 14, 2015

(65) Prior Publication Data

US 2016/0097108 A1   Apr. 7, 2016

Related U.S. Application Data

(63) Continuation of application No. 13/339,661, filed on Dec. 29, 2011, now Pat. No. 9,212,104.

(60) Provisional application No. 61/428,461, filed on Dec. 30, 2010.

(51) Int. Cl.

| | | |
|---|---|---|
| *C13K 13/00* | (2006.01) | |
| *C10G 1/06* | (2006.01) | |
| *C10G 3/00* | (2006.01) | |
| *C07B 63/00* | (2006.01) | |
| *C08B 30/12* | (2006.01) | |
| *B01J 20/34* | (2006.01) | |
| *C07C 29/132* | (2006.01) | |
| *B01J 23/46* | (2006.01) | |
| *B01J 23/652* | (2006.01) | |
| *B01J 23/68* | (2006.01) | |

(52) U.S. Cl.
CPC .............. *C13K 13/00* (2013.01); *C07B 63/00* (2013.01); *C08B 30/12* (2013.01); *C10G 1/06* (2013.01); *C10G 1/065* (2013.01); *C10G 3/42* (2013.01); *C10G 3/47* (2013.01); *B01J 20/34* (2013.01); *B01J 23/462* (2013.01); *B01J 23/464* (2013.01); *B01J 23/6527* (2013.01); *B01J 23/687* (2013.01); *C07C 29/132* (2013.01); *C10G 2300/1011* (2013.01); *C10G 2300/1014* (2013.01); *C10G 2300/44* (2013.01); *C10G 2300/805* (2013.01); *C10G 2400/30* (2013.01); *Y02P 30/20* (2015.11); *Y02P 30/42* (2015.11)

(58) Field of Classification Search
CPC ...................................................... C13K 13/00
See application file for complete search history.

(56) References Cited

U.S. PATENT DOCUMENTS

2012/0167876 A1* 7/2012 Qiao ...................... C10G 1/06
127/37

* cited by examiner

*Primary Examiner* — Melvin C Mayes
*Assistant Examiner* — Stefanie Cohen
(74) *Attorney, Agent, or Firm* — Quarles & Brady LLP

(57) ABSTRACT

The present invention provides processes for catalytic deconstruction of biomass using a solvent produced in a bioreforming reaction.

16 Claims, 8 Drawing Sheets

Figure 3. Catalytic biomass deconstruction using a byproduct stream from the BioForming process as an organic solvent.

Figure 5. Mass Balance and Feedstock Conversion of Organo-Catalytic Deconstruction

ORGANO-CATALYTIC BIOMASS DECONSTRUCTION

CROSS-REFERENCE TO RELATED APPLICATION

This application is a continuation of U.S. application Ser. No. 13/339,661, filed Dec. 29, 2011, now U.S. Pat. No. 9,212,104, which claims the benefit of U.S. Provisional Application No. 61/428,461 filed on Dec. 30, 2010.

FEDERAL FUNDING STATEMENT

This invention was made with government support under award #70NANB7H7023, requisition #4700558 awarded by NIST through the ATP program. The government has certain rights in the invention.

TECHNICAL FIELD

The present invention is directed to a process in which liquids produced in a bioreforming process are used in the solvent-facilitated catalytic deconstruction of biomass.

BACKGROUND OF THE INVENTION

The increasing cost of fossil fuel and environmental concerns have stimulated worldwide interest in developing alternatives to petroleum-based fuels, chemicals, and other products. Biomass materials are a possible renewable alternative.

Lignocellulosic biomass includes three major components. Cellulose, a primary sugar source for bioconversion processes, includes high molecular weight polymers formed of tightly linked glucose monomers. Hemicellulose, a secondary sugar source, includes shorter polymers formed of various sugars. Lignin includes phenylpropanoic acid moieties polymerized in a complex three dimensional structure. The resulting composition of lignocellulosic biomass is roughly 40-50% cellulose, 20-25% hemicellulose, and 25-35% lignin, by weight percent.

No cost-effective process currently exists for efficiently converting cellulose, hemicellulose, and lignin to components better suited for producing fuels, chemicals, and other products. This is generally because each of the lignin, cellulose and hemicellulose components demand distinct processing conditions, such as temperature, pressure, catalysts, reaction time, etc., in order to effectively break apart its polymer structure.

One can use expensive organic solvents such as acetone, ethanol, 4-methyl-2-pentanone, and solvent mixtures, to fractionate lignocellulosic biomass into cellulose, hemicellulose, and lignin streams (Paszner 1984; Muurinen 2000; and Bozell 1998). Using this process, the organic solvents dissolve some of the lignin such that it is possible to separate the dissolved lignin from the solid cellulose and hemicellulose. To the extent that the lignin can be separated, it can be burned for energy or can be converted with a ZSM-5 catalyst to liquid fuel compounds, such as benzene, toluene, and xylene (Thring 2000).

After removing the lignin from biomass, one can depolymerize the delignified lignocellulose by acid catalytic hydrolysis using acids such as sulfuric acid, phosphoric acid, and organic acids. Acid catalytic hydrolysis produces a hydrolysate product containing sugars, acid, and other components such as polyols, oligosaccharides, organic acids, lignin, and proteins. The hydrolysates can be separated using known fractionation processes. One can alternatively employ a specialized acid catalytic hydrolysis technology developed by Arkenol, Inc. to convert cellulose and hemicellulose in biomass to sugars using highly concentrated acid and to separate sugars from acid using a simulated moving bed process (Farone 1996).

Cellulose and hemicellulose can be used as feedstock for various bioreforming processes, including aqueous phase reforming (APR) and hydrodeoxygenation (HDO)—catalytic reforming processes that, when integrated with hydrogenation, can convert cellulose and hemicellulose into hydrogen and hydrocarbons, including liquid fuels and other chemical products. APR and HDO methods and techniques are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); and U.S. Pat. Nos. 7,767,867 and 7,989,664 and U.S. Application Ser. No. 2011/0306804 (all to Cortright, and entitled "Methods and Systems for Generating Polyols"). Various APR and HDO methods and techniques are described in U.S. Patent Application Ser. Nos. 2008/0216391; 2008/0300434; and 2008/0300435 (all to Cortright and Blommel, and entitled "Synthesis of Liquid Fuels and Chemicals from Oxygenated Hydrocarbons"); U.S. Patent Application Ser. No. 2009/0211942 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

Biomass must be deconstructed to less complex oxygenated compounds prior to use as feedstock for bioreforming processes. There remains a need for cost-effective methods for separating biomass into streams suitable for use in APR, HDO and other bioreforming processes.

SUMMARY

The invention provides methods for making a biomass hydrolysate. The method generally involves: (1) catalytically reacting water and a water-soluble $C_{2+}O_{1+}$ oxygenated hydrocarbon in a liquid or vapor phase with $H_2$ in the presence of a deoxygenation catalyst at a deoxygenation temperature and deoxygenation pressure to produce a biomass processing solvent comprising a $C_{2+}O_{1-3}$ hydrocarbon in a reaction stream; and (2) reacting the biomass processing solvent with a biomass component, hydrogen and a deconstruction catalyst at a deconstruction temperature and a deconstruction pressure to produce a biomass hydrolysate comprising at least one member selected from the group consisting of a water-soluble lignocellulose derivative, a water-soluble cellulose derivative, a water-soluble hemicellulose derivative, a carbohydrate, a starch, a monosaccharide, a disaccharide, a polysaccharide, a sugar, a sugar alcohol, an alditol and a polyol.

One aspect of the invention is the composition of the biomass processing solvent. In one embodiment, the biomass processing solvent includes a member selected from the group consisting of an alcohol, ketone, aldehyde, cyclic ether, ester, diol, triol, hydroxy carboxylic acid, carboxylic acid, and a mixture thereof.

The biomass processing solvent is produced in the presence of a deconstruction catalyst. In one embodiment, the deconstruction catalyst comprises an acidic resin or a basic resin. The deconstruction catalyst may further comprise a member selected from the group consisting of Fe, Co, Ni, Cu, Ru, Rh, Pd, Pt, Re, Mo, W, alloys thereof, and combinations thereof, or a support and a member adhered to the support selected from the group consisting of Cu, Fe, Ru, Ir, Co, Rh, Pt, Pd, Ni, W, Mo alloys thereof, and combinations thereof. In another embodiment, the deconstruction catalyst may further comprise a member selected from the group consisting of Cu, Mn, Cr, Mo, B, W, V, Nb, Ta, Ti, Zr, Y, La, Sc, Zn, Cd, Ag, Au, Sn, Ge, P, Al, Ga, In, Tl, alloys thereof, and combinations thereof.

In one embodiment, the oxygenated hydrocarbon is selected from the group consisting of a starch, a carbohydrate, a polysaccharide, a disaccharide, a monosaccharide, a sugar, a sugar alcohol, a alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, and a polyol.

The invention also provides a method of making a biomass hydrolysate comprising the steps of: (1) catalytically reacting water and a water-soluble $C_{2+}O_{1+}$ oxygenated hydrocarbon in a liquid or vapor phase with $H_2$ in the presence of a deoxygenation catalyst at a deoxygenation temperature and deoxygenation pressure to produce an oxygenate comprising a $C_{2+}O_{1-3}$ hydrocarbon in a reaction stream; (2) catalytically reacting in the liquid or vapor phase the oxygenate in the presence of a condensation catalyst at a condensation temperature and condensation pressure to produce a biomass processing solvent comprising one or more $C_{4+}$ compounds; and (3) reacting the biomass processing solvent with a biomass component, hydrogen and a deconstruction catalyst at a deconstruction temperature and a deconstruction pressure to produce a biomass hydrolysate comprising at least one member selected from the group consisting of a water-soluble lignocellulose derivative, a water-soluble cellulose derivative, a water-soluble hemicellulose derivative, a carbohydrate, a starch, a monosaccharide, a disaccharide, a polysaccharide, a sugar, a sugar alcohol, an alditol, and a polyol.

The biomass processing solvent may include a member selected from the group consisting of an alkane, alkene and an aromatic. In one embodiment, the member is selected from the group consisting of benzene, toluene and xylene.

The deconstruction catalyst may comprise an acidic resin or a basic resin. In one embodiment, the deconstruction catalyst further comprises a member selected from the group consisting of Fe, Co, Ni, Cu, Ru, Rh, Pd, Pt, Re, Mo, W, alloys thereof, and combinations thereof. The deconstruction catalyst may also comprise a support and a member adhered to the support selected from the group consisting of Cu, Fe, Ru, Ir, Co, Rh, Pt, Pd, Ni, W, Mo, alloys thereof and combinations thereof, or it may further comprise a member selected from the group consisting of Cu, Mn, Cr, Mo, B, W, V, Nb, Ta, Ti, Zr, Y, La, Sc, Zn, Cd, Ag, Au, Sn, Ge, P, Al, Ga, In, Tl, alloys thereof and combinations thereof.

In one embodiment, the $C_{2+}O_{1+}$ hydrocarbon is selected from the group consisting of a starch, a carbohydrate, a polysaccharide, a disaccharide, a monosaccharide, a sugar, a sugar alcohol, an alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, and a polyol.

The condensation catalyst may comprise a member selected from the group consisting of a carbide, a nitride, zirconia, alumina, silica, an aluminosilicate, a phosphate, a zeolite, a titanium oxide, a zinc oxide, a vanadium oxide, a lanthanum oxide, a yttrium oxide, a scandium oxide, a magnesium oxide, a cerium oxide, a barium oxide, a calcium oxide, a hydroxide, a heteropolyacid, an inorganic acid, an acid modified resin, a base modified resin, and combinations thereof.

The invention also provides a method of deconstructing biomass. The method generally includes reacting a biomass slurry with a biomass processing solvent comprising a $C_{2+}O_{1-3}$ hydrocarbon at a deconstruction temperature between about 80° C. and 350° C. and a deconstruction pressure between about 100 psi and 2000 psi to produce a biomass hydrolysate comprising at least one member selected from the group consisting of a water-soluble lignocellulose derivative, water-soluble cellulose derivative, water-soluble hemicellulose derivative, carbohydrate, starch, monosaccharide, disaccharide, polysaccharide, sugar, sugar alcohol, alditol, and polyol, wherein the biomass processing solvent is produced by catalytically reacting in the liquid or vapor phase an aqueous feedstock solution comprising water and a water-soluble oxygenated hydrocarbons comprising a $C_{2+}O_{1+}$ hydrocarbon with $H_2$ in the presence of a deoxygenation catalyst at a deoxygenation temperature and deoxygenation pressure.

In one embodiment, the $H_2$ comprises at least one of an in situ-generated $H_2$, external $H_2$, or recycled $H_2$. The $H_2$ may comprise $H_2$ generated in situ by catalytically reacting in a liquid phase or vapor phase a portion of the water and the oxygenated hydrocarbon in the presence of an aqueous phase reforming catalyst at a reforming temperature and reforming pressure.

In one embodiment, the oxygenated hydrocarbon comprises a member selected from the group consisting of a lignocellulose derivative, a cellulose derivative, a hemicellulose derivative, a carbohydrate, a starch, a monosaccharide, a disaccharide, a polysaccharide, a sugar, a sugar alcohol, an alditol, and a polyol. The biomass hydrolysate may be recycled and combined with the biomass slurry.

One aspect of the invention is the biomass processing solvent which may comprise a member selected from the group consisting of an alcohol, ketone, aldehyde, cyclic ether, ester, diol, triol, hydroxy carboxylic acid, carboxylic acid, and a mixture thereof. In one embodiment, biomass processing solvent comprises a member selected from the group consisting of ethanol, n-propyl alcohol, isopropyl alcohol, butyl alcohol, pentanol, hexanol, cyclopentanol, cyclohexanol, 2-methylcyclopentanol, a hydroxyketone, a cyclic ketone, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, a hydroxyaldehyde, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2,5-dimethyl furan, 2-ethyl furan, hydroxylmethylfurfural, 3-hydroxytetrahydrofuran, tetrahydro-3-furanol, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, and hydroxymethyltetrahydrofurfural, isomers thereof, and combinations thereof.

The deoxygenation catalyst is capable of deoxygenating water-soluble oxygenated hydrocarbons to produce the biomass processing solvent. In one embodiment, the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, and a combination thereof. The deoxygenation catalyst may further comprise a member selected from the group consisting of Mn, Cr, Mo, W, V, Nb, Ta, Ti, Zr, Y, La, Sc, Zn, Cd, Ag, Au, Sn, Ge, P, Al, Ga, In, Tl, and a combination thereof. The deoxygenation catalyst may have an active metal function and an acidic function. The support may comprise a member selected from group consisting of a carbon, silica, alumina, zirconia, titania, tungsten, vanadia, heteropolyacid, kieselguhr, hydroxyapatite, chromia, zeolites, and mixtures thereof. The support may be a member selected from the group consisting of tungstated zirconia, tungsten modified zirconia, tungsten modified alpha-alumina, or tungsten modified theta alumina.

In one embodiment, the aqueous phase reforming catalyst comprises a support and a member selected from the group consisting of Fe, Ru, Ir, Co, Rh, Pt, Pd, Ni, an alloy thereof, and a combination thereof. The aqueous phase reforming catalyst may further comprise a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, an alloy thereof, and a combination thereof. In another embodiment, the aqueous phase reforming catalyst and the deoxygenation catalyst are combined into a single catalyst.

The aqueous phase reforming and deoxygenation reactions are conducted at a temperature and pressure where the thermodynamics are favorable. In one embodiment, the reforming temperature is in the range of about 100° C. to about 450° C. or about 100° C. to about 300° C., and the reforming pressure is a pressure where the water and the oxygenated hydrocarbon are gaseous. In another embodiment, the reforming temperature is in the range of about 80° C. to 400° C., and the reforming pressure is a pressure where the water and the oxygenated hydrocarbon are liquid.

The deoxygenation temperature may be greater than 120° C., or 150° C., or 180° C., or 200° C., and less than 325° C., or 300° C., or 280° C., or 260° C., or 240° C., or 220° C. The deoxygenation pressure may be greater than 200 psig, or 365 psig, or 500 psig or 600 psig, and less than 2500 psig, or 2250 psig, or 2000 psig, or 1800 psig, or 1500 psig, or 1200 psig, or 1000 psig. The deoxygenation temperature may also be in the range of about 120° C. to 325° C., and the deoxygenation pressure is at least 0.1 atmosphere. In other embodiments, the deoxygenation temperature is in the range of about 120° C. to about 325° C. or about 200° C. to 280° C., and the deoxygenation pressure is between about 365 psig and about 2500 psig, or about 600 psig and 1800 psig.

In one embodiment, the APR catalyst and the deoxygenation catalyst are combined into a single catalyst. In this aspect, the reforming temperature and deoxygenation temperature may be in the range of about 100° C. to 325° C., or about 120° C. to 300° C., or about 200° C. to 280° C., and the reforming pressure and deoxygenation pressure may be in the range of about 200 psig to 1500 psig, or about 200 psig to 1200 psig, or about 200 psig to 725 psig.

In one aspect, the step of reacting a biomass slurry with a biomass processing solvent is performed in the same reactor as the step of catalytically reacting the aqueous feedstock solution with $H_2$ in the presence of a deoxygenation catalyst. The deconstruction temperature and deoxygenation temperature may be in the range of about 100° C. to 325° C., about 120° C. to 300° C., or about 200° C. to 280° C., and the deconstruction pressure and deoxygenation pressure may be in the range of about 200 psig to 1500 psig, about 200 psig to 1200 psig, or about 600 psig to 1800 psig.

The deconstruction catalyst includes an acidic resin or a basic resin and may include a member selected from the group consisting of Fe, Co, Ni, Cu, Ru, Rh, Pd, Pt, Re, Mo, W, and alloys thereof or a support and a member selected from the group consisting of Cu, Fe, Ru, Ir, Co, Rh, Pt, Pd, Ni, W, Mo, alloys thereof, and combinations thereof. The deconstruction catalyst may further comprise a member selected from the group consisting of Cu, Mn, Cr, Mo, B, W, V, Nb, Ta, Ti, Zr, Y, La, Sc, Zn, Cd, Ag, Au, Sn, Ge, P, Al, Ga, In, Tl, and alloys thereof.

Another aspect of the invention includes the step of dewatering the biomass hydrolysate.

DETAILED DESCRIPTION OF THE INVENTION

The present invention provides methods, reactor systems and catalysts for hydrolyzing or deconstructing biomass using a heterogeneous catalyst and a biomass processing solvent produced in a bioreforming process. The resulting product stream includes a biomass hydrolysate that can be further processed in a bioreforming process to provide the biomass processing solvent and a product stream for further conversion to desired compounds. The bioreforming process and deconstruction process may occur separately in different reactors or together in a single reactor, and generally occur in steady-state as part of a continuous process.

As used herein, the term "biomass" refers to, without limitation, organic materials produced by plants (such as leaves, roots, seeds and stalks), and microbial and animal metabolic wastes. Common biomass sources include: (1) agricultural residues, including corn stover, straw, seed hulls, sugarcane leavings, bagasse, nutshells, cotton gin trash, and manure from cattle, poultry, and hogs; (2) wood materials, including wood or bark, sawdust, timber slash, and mill scrap; (3) municipal solid waste, including recycled paper, waste paper and yard clippings; and (4) energy crops, including poplars, willows, switch grass, *miscanthus*, sorghum, alfalfa, prairie bluestream, corn, soybean, and the like. The term also refers to the primary building blocks of the above, namely, lignin, cellulose, hemicellulose and carbohydrates, such as saccharides, sugars and starches, among others.

As used herein, the term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, diols and other polyols, using aqueous phase reforming, hydrogenation, hydrogenolysis, hydrodeoxygenation and/or other conversion processes involving the use of heterogeneous catalysts. Bioreforming also includes the further catalytic conversion of such lower molecular weight oxygenated compounds to $C_{4+}$ compounds.

Figure 1:
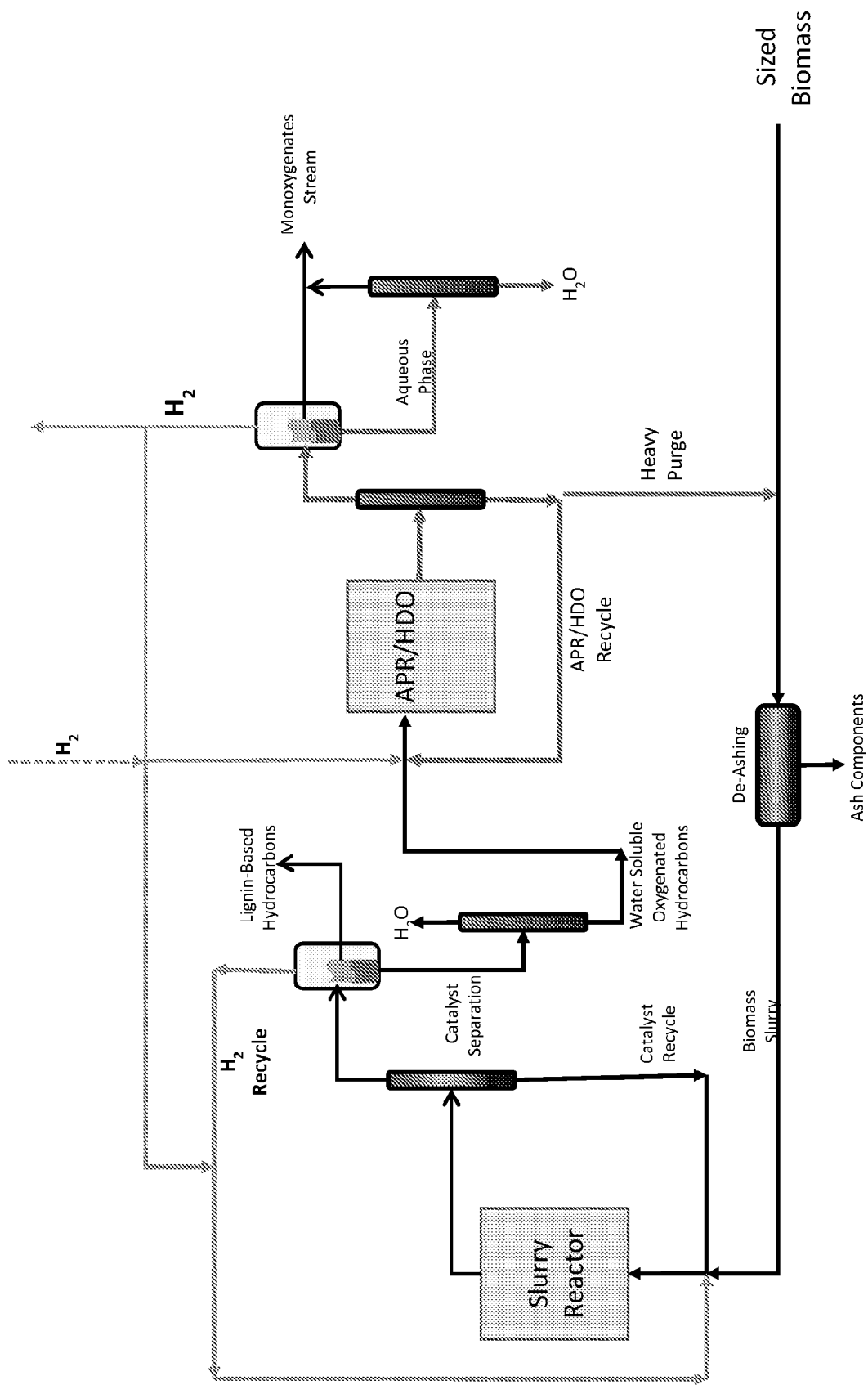
FIG. 1 is a flow diagram illustrating a process for catalytically converting biomass to liquid fuels using a biomass processing solvent derived from a recycle stream associated with the conversion of biomass hydrolysate in an APR/HDO process.
Figure 2:
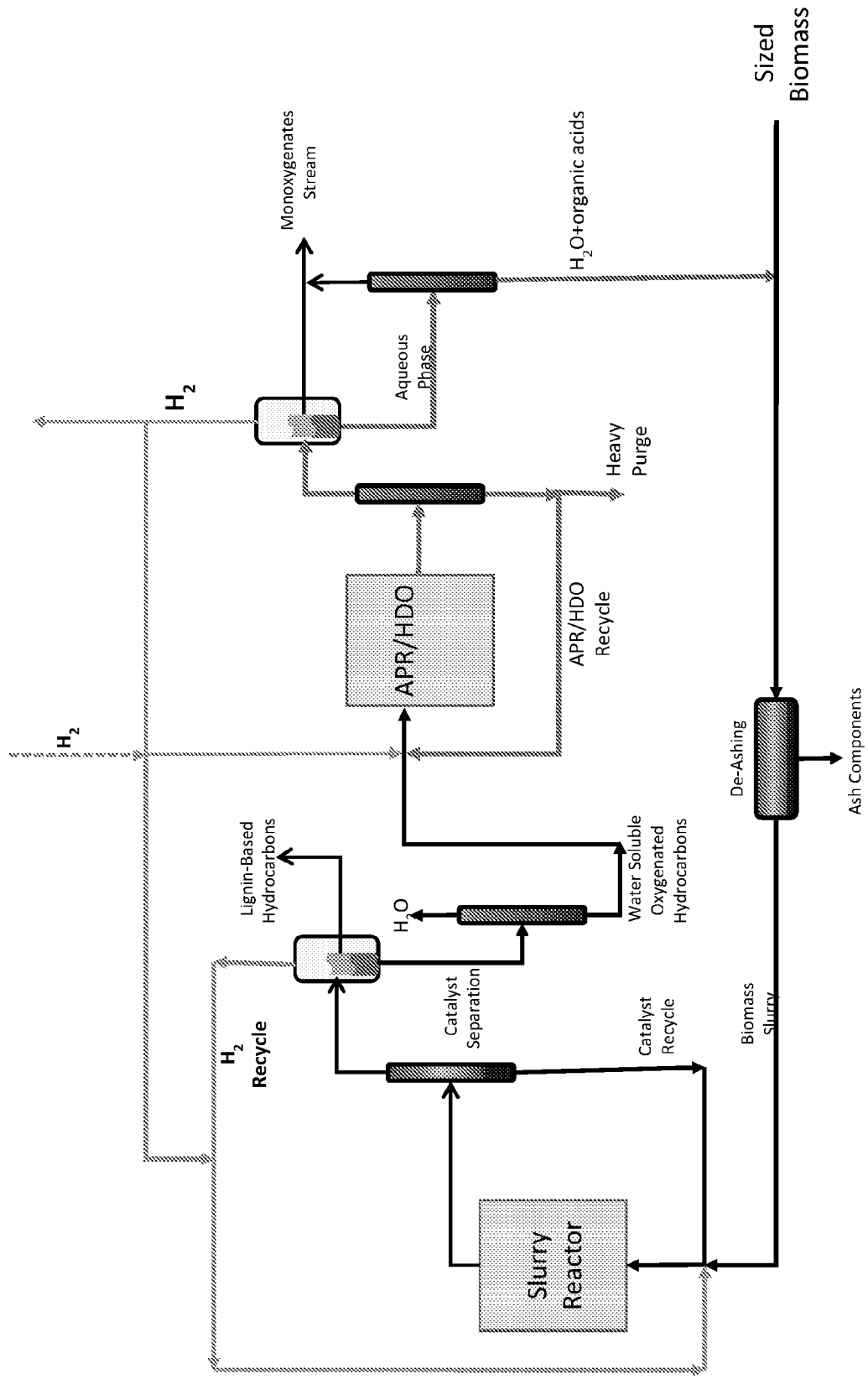
FIG. 2 is a flow diagram illustrating a process for catalytically converting biomass to liquid fuels using a biomass processing solvent derived the conversion of biomass hydrolysate in an APR/HDO process.

The deconstruction process uses hydrogen, a heterogeneous deconstruction catalyst and a biomass processing solvent or solvent mixture produced in a bioreforming process. One such process is illustrated in FIG. 1. First, in the deconstruction process, a biomass slurry is combined with a deconstruction catalyst, hydrogen and a biomass processing solvent or solvent mixture produced in a bioreforming process. The biomass slurry may include any type of biomass that has been chopped, shredded, pressed, ground or processed to a size amenable for conversion. The biomass processing solvent or solvent mixture may contain a wide range of oxygenates, such as ketones, alcohols, cyclic ethers, acids, and esters, and/or $C_{4+}$ hydrocarbons, such as $C_{4+}$ alkanes, $C_{4+}$ alkenes, and aromatic compounds, including benzene, toluene, xylene. In a preferred embodiment, the biomass processing solvent or solvent mixture is derived from the biomass hydrolysate or, as illustrated in FIGS. 1 and 2, from the further processing of the biomass hydrolysate in a bioreforming process.

The deconstruction catalyst is a heterogeneous catalyst having one or more materials capable of catalyzing a reaction between hydrogen and lignin, cellulose, hemicellulose and their derivatives to produce the desired oxygenated compounds. The heterogeneous deconstruction catalyst may include, without limitation, acid modified resin, base modified resin, and/or one or more of Cu, Fe, Ru, Ir, Co, Rh, Pt, Pd, Ni, W, Mo, alloys and combinations thereof. The deconstruction catalyst may include these elements alone or combined with one or more Cu, Mn, Cr, Mo, B, W, V, Nb, Ta, Ti, Zr, Y, La, Sc, Zn, Cd, Ag, Au, Sn, Ge, P, Al, Ga, In, Tl, Ce and combinations thereof. In one embodiment, the deconstruction catalyst includes Ni, Ru, Ir, Pt, Pd, Rh, Co, or Mo and at least one member selected from W, B, Pt, Sn, Ag, Au, Rh, Co, and Mo.

Resins will generally include basic or acidic supports (e.g., supports having low isoelectric points) that are able to catalyze deconstruction reactions of biomass, followed by hydrogenation reactions in the presence of $H_2$, leading to carbon atoms that are not bonded to oxygen atoms. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, and $H_6P2W_{18}O_{62}$. Heteropolyacids also have a well-defined local structure, the most common of which is the tungsten-based Keggin structure. Basic resins include resins that exhibit basic functionality, such as Amberlyst.

The deconstruction catalyst is either self-supporting or includes a supporting material. The support may contain any one or more of nitride, carbon, silica, alumina, zirconia, titania, tungsten, vanadia, ceria, zinc oxide, chromia, boron nitride, tungstated zirconia, heteropolyacids, kieselguhr, hydroxyapatite, and mixtures thereof. Preferable supports are carbon, m-$ZrO_2$, and W—$ZrO_2$. In one embodiment, the deconstruction catalyst includes Ni:Mo, Pd:Mo, Rh:Mo, Co:Mo, Pd:Ru, Pt:Re, or Pt:Rh on a m-$ZrO_2$ support. In another embodiment, the deconstruction catalyst includes Ru, Ru:Pt, Pd:Ru, Pt:Re, Pt:Rh, Pd:Mo, Pd:Ag, or Ru:Pt:Sn on a carbon or W—$ZrO_2$ support. In yet another embodiment the deconstruction catalyst includes Fe, Co, Ni, Cu, Ru, Rh, Pd, Pt, Re, Mo, or W on a carbon support. The support may also serve as a functional catalyst, such as in the case of acidic or basic resins or supports having acidic or basic functionality.

In one embodiment, the deconstruction catalyst is formed in a honeycombed monolith design such that the biomass slurry, solid phase slurry or the solid/liquid phase slurry can flow through the deconstruction catalyst. In another embodiment, the deconstruction catalyst includes a magnetic element such as Fe or Co such that the deconstruction catalyst can be easily separated from the resulting product mixture.

The product stream resulting from the biomass deconstruction will generally include water, unreacted or under-reacted product, ash and a biomass hydrolysate that includes lignin and lignocellulosic derivatives, cellulose and cellulosic derivatives, hemicellulose and hemicellulosic derivatives, carbohydrates, starches, monosaccharides, disaccharides, polysaccharides, sugars, sugar alcohols, alditols, polyols and mixtures thereof. Preferably, the biomass hydrolysate includes sugar, sugar alcohols, starch, saccharides and other polyhydric alcohols. More preferably, the biomass hydrolysate includes a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, arabitol, or glycol. In certain embodiments, the biomass hydrolysate may also include alcohols, ketones, cyclic ethers, esters, carboxylic acids, aldehydes, diols and other polyols that are useful as the processing solvent. In other embodiments, the biomass hydrolysate may also include mono-oxygenated hydrocarbons that may be further converted to $C_{4+}$ hydrocarbons, such as $C_{4+}$ alkanes, $C_{4+}$ alkenes, and aromatic compounds, including benzene, toluene, xylene, which are useful as liquid fuels and chemicals.

The resulting biomass hydrolysate may be collected for further processing in a bioreforming process or, alternatively, used as a feedstock for other conversion processes, including the production of fuels and chemicals using fermentation or enzymatic technologies. For example, water-soluble carbohydrates, such as starch, monosaccharides, disaccharides, polysaccharides, sugars, and sugar alcohols, and water-soluble derivatives from the lignin, hemicellulose and cellulose are suitable for use in bioreforming processes. Alternatively, the resulting biomass hydrolysate may be recycled and combined in the biomass slurry for further conversion or use as a processing solvent.

In certain applications, the biomass product stream undergoes one or more separation steps to separate the ash, unreacted biomass and under-reacted biomass from the product stream to provide the biomass hydrolysate. The biomass hydrolysate may also require further processing to separate aqueous phase products from organic phase products, such as lignin-based hydrocarbons not suitable for bioreforming processes. The biomass hydrolysate may also be dewatered or further purified prior to being introduced into the bioreforming process. Such dewatering and purification processes are known in the art and may include simulated moving bed technology, distillation, filtration, etc.

Biomass Processing Solvent

Bioreforming processes convert starches, sugars and other polyols to a wide range of oxygenates, including organic compounds that facilitate biomass deconstruction. As used herein, "oxygenates" generically refers to hydrocarbon compounds having 2 or more carbon atoms and 1, 2 or 3 oxygen atoms (referred to herein as $C_{2+}O_{1-3}$ hydrocarbons), such as alcohols, ketones, aldehydes, cyclic ethers, hydroxy carboxylic acids, carboxylic acids, diols and triols. Preferably, the oxygenates have from 2 to 6 carbon atoms, or 3 to 6 carbon atoms. Alcohols may include, without limitation, primary, secondary, linear, branched or cyclic $C_{2+}$ alcohols, such as ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. The diols may include, without limitation, lactones, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1, 1, 1 tris(hydroxymethyl)-ethane (trimethylolethane), trim ethylolpropane, hexanetriol, and isomers thereof. Cyclic ethers include, without limitation, furfural, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl) ethanol, hydroxymethyltetrahydrofurfural, and isomers thereof.

The above oxygenates may originate from any source, but are preferably derived from oxygenated hydrocarbons resulting from the initial processing of the biomass in the biomass slurry. Oxygenated hydrocarbons may be any water-soluble oxygenated hydrocarbon having two or more carbon atoms and at least one oxygen atom (referred to herein as $C_{2+}O_{1+}$ hydrocarbons). Preferably, the oxygenated hydrocarbon has 2 to 12 carbon atoms ($C_{1-12}O_{1-11}$ hydrocarbon), and more preferably 2 to 6 carbon atoms ($C_{1-6}O_{1-6}$ hydrocarbon), and 1, 2, 3, 4, 5 or 6 oxygen atoms. The oxygenated hydrocarbon may also have an oxygen-to-carbon ratio ranging from 0.5:1 to 1.5:1, including ratios of 0.75:1.0, 1.0:1.0, 1.25:1.0, 1.5:1.0, and other ratios between. In one example, the oxygenated hydrocarbon has an oxygen-to-carbon ratio of 1:1. Nonlimiting examples of preferred water-soluble oxygenated hydrocarbons include starches, monosaccharides, disaccharides, polysaccharides, sugar, sugar alcohols, alditols, ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tautaric acid, aldopentoses, aldohexoses, ketotetroses, ketopentoses, ketohexoses, alditols, hemicelluloses, cellulosic derivatives, lignocellulosic derivatives, starches, polyols and the like. Preferably, the oxygenated hydrocarbon includes starches, sugar, sugar alcohols, saccharides and other polyhydric alcohols. More preferably, the oxygenated hydrocarbon is a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, ribitol, or glycol.

Production of the Biomass Processing Solvent

As shown in Table 1 below, the bioreforming process produces a complex organic mixture. The mixture of different organics provides good candidate compounds for a high quality biomass deconstruction solvent.

TABLE 1

Typical Products of a Bioreforming Process

| Aqueous Phase | | Organic Phase | |
| --- | --- | --- | --- |
| Component | % of Phase | Component | % of Phase |
| 2-Pentanone | 13.75 | 3-Hexanone | 12.98 |
| Butanoic acid | 13.61 | 2-Hexanone | 12.60 |
| 2-Butanone | 13.08 | 2-Pentanone | 9.53 |
| Furan, tetrahydro-2,5-dimethyl- | 10.70 | Water | 6.64 |
| | | Butanoic acid | 6.19 |
| Acetone | 8.43 | 2-Furanmethanol, tetrahydro- | 5.68 |
| Propionic Acid | 8.15 | Furan, tetrahydro-2,5-dimethyl- | 5.29 |
| Acetic acid | 4.82 | 3-Pentanone | 4.93 |
| Pentanoic acid | 4.68 | Pentanoic acid | 4.41 |
| 2-Butanol, (.+/−.)- | 3.77 | 2-Butanone | 4.35 |
| 2-Hexanone | 3.75 | 2H-Pyran, tetrahydro-2-methyl- | 2.78 |
| 3-Hexanone | 3.57 | 2-Hexanol | 2.22 |
| (R)-(−)-2-Pentanol | 1.82 | Hexanoic acid | 2.10 |
| Isopropyl Alcohol | 1.73 | Furan, tetrahydro-2-methyl- | 1.95 |

TABLE 1-continued

Typical Products of a Bioreforming Process

| Aqueous Phase | | Organic Phase | |
|---|---|---|---|
| Component | % of Phase | Component | % of Phase |
| Hexanoic acid | 1.09 | 2(3H)-Furanone, 5-ethyldihydro- | 1.71 |
| 2-Butanone, 3-hydroxy- | 1.05 | | |
| | | 2-Pentanol | 1.71 |
| | | 3-Hexanol | 1.62 |
| | | Hexane | 1.55 |
| | | Pentane | 1.52 |
| | | Propionic Acid | 1.42 |

The oxygenates are prepared by reacting an aqueous feedstock solution containing water and the water-soluble oxygenated hydrocarbons with hydrogen over a catalytic material to produce the desired oxygenates. The hydrogen may be generated in situ using aqueous phase reforming (in situ generated $H_2$ or APR $H_2$), or a combination of APR $H_2$, external $H_2$ or recycled $H_2$, or just simply external $H_2$ or recycled $H_2$. The term "external $H_2$" refers to hydrogen that does not originate from the feedstock solution, but is added to the reactor system from an external source. The term "recycled $H_2$" refers to unconsumed hydrogen, which is collected and then recycled back into the reactor system for further use. External $H_2$ and recycled $H_2$ may also be referred to collectively or individually as "supplemental $H_2$." In general, supplemental $H_2$ may be added for purposes of supplementing the APR hydrogen or to increase the reaction pressure within the system, or to increase the molar ratio of hydrogen to carbon and/or oxygen in order to enhance the production yield of certain reaction product types, such as ketones and alcohols.

In processes utilizing APR $H_2$, the oxygenates are prepared by catalytically reacting a portion of the aqueous feedstock solution containing water and the water-soluble oxygenated hydrocarbons in the presence of an APR catalyst at a reforming temperature and reforming pressure to produce the APR $H_2$, and catalytically reacting the APR $H_2$ (and recycled $H_2$ and/or external $H_2$) with a portion of the feedstock solution in the presence of a deoxygenation catalyst at a deoxygenation temperature and deoxygenation pressure to produce the desired oxygenates. In systems utilizing recycled $H_2$ or external $H_2$ as a hydrogen source, the oxygenates are simply prepared by catalytically reacting the recycled $H_2$ and/or external $H_2$ with the feedstock solution in the presence of the deoxygenation catalyst at the deoxygenation temperatures and pressures. In each of the above, the oxygenates may also include recycled oxygenates (recycled $C_{1+}O_{1-3}$ hydrocarbons).

The deoxygenation catalyst is preferably a heterogeneous catalyst having one or more active materials capable of catalyzing a reaction between hydrogen and the oxygenated hydrocarbon to remove one or more of the oxygen atoms from the oxygenated hydrocarbon to produce alcohols, ketones, aldehydes, cyclic ethers, carboxylic acids, hydroxy carboxylic acids, diols and triols. In general, the heterogeneous deoxygenation catalyst will have both an active metal function and an acidic function to achieve the foregoing. For example, acidic supports (e.g., supports having low isoelectric points) first catalyze dehydration reactions of oxygenated compounds. Hydrogenation reactions then occur on the metallic catalyst in the presence of $H_2$, producing carbon atoms that are not bonded to oxygen atoms. The bi-functional dehydration/hydrogenation pathway consumes $H_2$ and leads to the subsequent formation of various polyols, diols, ketones, aldehydes, alcohols, carboxylic acids, hydroxy carboxylic acids and cyclic ethers, such as furans and pyrans.

The active materials may include, without limitation, Cu, Re, Fe, Ru, Ir, Co, Rh, Pt, Pd, Ni, W, Os, Mo, Ag, Au, alloys thereof, and combinations thereof, adhered to a support. The deoxygenation catalyst may include these elements alone or in combination with one or more Mn, Cr, Mo, W, V, Nb, Ta, Ti, Zr, Y, La, Sc, Zn, Cd, Ag, Au, Sn, Ge, P, Al, Ga, In, Tl, Ce, and combinations thereof. In one embodiment, the deoxygenation catalyst includes Pt, Pd, Ru, Re, Ni, W or Mo. In yet another embodiment, the deoxygenation catalyst includes Sn, W, Mo, Ag, Fe and/or Re and at least one transition metal selected from Ni, Pd, Pt and Ru. In another embodiment, the catalyst includes Fe, Re and at least Cu or one Group VIIIB transition metal. In yet another embodiment, the deoxygenation catalyst includes Pd alloyed or admixed with Cu or Ag and supported on an acidic support. In yet another embodiment, the deoxygenation catalyst includes Pd alloyed or admixed with a Group VIB metal supported on an acidic support. In yet another embodiment, the deoxygenation catalyst includes Pd alloyed or admixed with a Group VIB metal and a Group IVA metal on an acidic support. The support may be any one of a number of supports, including a support having carbon, silica, alumina, zirconia, titania, tungsten, vanadia, chromia, zeolites, heteropolyacids, kieselguhr, hydroxyapatite, and mixtures thereof.

The deoxygenation catalyst may also include an acidic support modified or constructed to provide the desired functionality. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, and $H_6P2W_{18}O_{62}$. Heteropolyacids are solid-phase acids having a well-defined local structure, the most common of which is the tungsten-based Keggin structure. Other examples may include, without limitation, tungstated zirconia, tungsten modified zirconia, tungsten modified alpha-alumina, or tungsten modified theta alumina.

Loading of the first element (i.e., Cu, Re, Fe, Ru, Ir, Co, Rh, Pt, Pd, Ni, W, Os, Mo, Ag, Au, alloys and combinations thereof) is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second element (i.e., Mn, Cr, Mo, W, V, Nb, Ta, Ti, Zr, Y, La, Sc, Zn, Cd, Ag, Au, Sn, Ge, P, Al, Ga, In, Tl, Ce, and combinations thereof) is in the range of 0.25-to-1 to 10-to-1, including any ratios between, such as 0.50, 1.00, 2.50, 5.00, and 7.50-to-1. If the catalyst is adhered to a support, the combination of the catalyst and the support is from 0.25 wt % to 10 wt % of the primary element.

To produce oxygenates, the oxygenated hydrocarbon is combined with water to provide an aqueous feedstock solution having a concentration effective for causing the formation of the desired reaction products. The water-to-carbon ratio on a molar basis is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included. Preferably the balance of the feedstock solution is water. In some embodiments, the feedstock solution consists essentially of water, one or more oxygenated hydrocarbons and, optionally, one or more feedstock modifiers described herein, such as alkali or hydroxides of alkali or alkali earth salts or acids. The feedstock solution may also include recycled oxygenated hydrocarbons recycled from the reactor system. The feedstock solution may also contain negligible amounts of hydrogen, preferably less than about 1.5 mole of hydrogen per mole of feedstock.

The feedstock solution is reacted with hydrogen in the presence of the deoxygenation catalyst at deoxygenation temperature and pressure conditions, and weight hourly space velocity, effective to produce the desired oxygenates. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the catalysts over time, will limit the extent of the reactions which may occur, thereby causing increased yield for higher level diols and triols, with a reduction in ketone and alcohol yields.

The deoxygenation temperature and pressure are preferably selected to maintain at least a portion of the feedstock in the liquid phase at the reactor inlet. It is recognized, however, that temperature and pressure conditions may also be selected to more favorably produce the desired products in the vapor-phase or in a mixed phase having both a liquid and vapor phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In general, the deoxygenation temperature should be greater than 120° C., or 150° C., or 180° C., or 200° C., and less than 325° C., or 300° C., or 280° C., or 260° C., or 240° C., or 220° C. The reaction pressure should be greater than 200 psig, or 365 psig, or 500 psig or 600 psig, and less than 2500 psig, or 2250 psig, or 2000 psig, or 1800 psig, or 1500 psig, or 1200 psig, or 1000 psig, or 725 psig. In one embodiment, the deoxygenation temperature is between about 150° C. and 300° C., or between about 200° C. and 280° C., or between about 220° C. and 260° C., or between about 150° C. and 260° C. In another embodiment, the deoxygenation pressure is between about 365 and 2500 psig, or between about 500 and 2000 psig, or between about 600 and 1800 psig, or between about 365 and 1500 psig.

A condensed liquid phase method may also be performed using a modifier that increases the activity and/or stability of the catalyst system. It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the catalyst system used, although amounts outside this range are included within the present invention.

In general, the reaction should be conducted under conditions where the residence time of the feedstock solution over the catalyst is appropriate to generate the desired products. For example, the WHSV for the reaction may be at least about 0.1 gram of oxygenated hydrocarbon per gram of catalyst per hour, and more preferably the WHSV is about 0.1 to 40.0 g/g hr, including a WHSV of about 0.25, 0.5, 0.75, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.83, 0.85, 0.85, 1.71, 1.72, 1.73, etc.).

The hydrogen used in the deoxygenation reaction may be in-situ-generated $H_2$, external $H_2$ or recycled $H_2$. The amount (moles) of external $H_2$ or recycled $H_2$ introduced to the feedstock is between 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-2%, or 0-1% of the total number of moles of the oxygenated hydrocarbon(s) in the feedstock, including all intervals between. When the feedstock solution, or any portion thereof, is reacted with APR hydrogen and external $H_2$ or recycled $H_2$, the molar ratio of APR hydrogen to external $H_2$ (or recycled $H_2$) is at least 1:100, 1:50, 1:20; 1:15, 1:10, 1:5; 1:3, 1:2, 1:1, 2:1, 3:1, 5:1, 10:1, 15:1, 20:1, 50:1, 100:1 and ratios between (including 4:1, 6:1, 7:1, 8:1, 9:1, 11:1, 12:1, 13:1, 14:1, 15:1, 16:1, 17:1, 18:1 and 19:1, and vice-versa).

In-situ Hydrogen Production

One advantage of the present invention is that it allows for the production and use of in-situ-generated $H_2$. The APR $H_2$ is produced from the feedstock under aqueous phase reforming conditions using an aqueous phase reforming catalyst (APR catalyst). The APR catalyst is preferably a heterogeneous catalyst capable of catalyzing the reaction of water and oxygenated hydrocarbons to form $H_2$ under the conditions described below. In one embodiment, the APR catalyst includes a support and at least one Group VIIIB metal, Fe, Ru, Ir, Co, Rh, Pt, Pd, Ni, alloys and combinations thereof. The APR catalyst may also include at least one additional material from Group VIIIB, Group VIIB, Group VIB, Group VB, Group IVB, Group IIB, Group IB, Group IVA or Group VA metals, such as Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce alloys and combinations thereof. The preferred Group VIM metal includes Re, Mn, or combinations thereof. The preferred Group VIB metal includes Cr, Mo, W, or a combination thereof. The preferred Group VIIIB metals include Pt, Rh, Ru, Pd, Ni, or combinations thereof. The supports may include any one of the catalyst supports described below, depending on the desired activity of the catalyst system.

The APR catalyst may also be atomically identical to the deoxygenation catalyst. For instance, the APR and deoxygenation catalyst may include Pt alloyed or admixed with Ni, Ru, Cu, Fe, Rh, Re, alloys and combinations thereof. The APR catalyst and deoxygenation catalyst may also include Ru alloyed or admixed with Ge, Bi, B, Ni, Sn, Cu, Fe, Rh, Pt, alloys and combinations thereof. The APR catalyst may also include Ni alloyed or admixed with Sn, Ge, Bi, B, Cu, Re, Ru, Fe, alloys and combinations thereof.

Preferred loading of the primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second material is in the range of 0.25-to-1 to 10-to-1, including ratios between, such as 0.50, 1.00, 2.50, 5.00, and 7.50-to-1.

A preferred catalyst composition is further achieved by the addition of oxides of Group IIIB, and associated rare earth oxides. In such event, the preferred components would be oxides of either lanthanum or cerium. The preferred atomic ratio of the Group IIIB compounds to the primary Group VIIIB metal is in the range of 0.25-to-1 to 10-to-1, including ratios between, such as 0.50, 1.00, 2.50, 5.00, and 7.50-to-1.

Another preferred catalyst composition is one containing platinum and rhenium. The preferred atomic ratio of Pt to Re is in the range of 0.25-to-1 to 10-to-1, including ratios there-between, such as 0.50, 1.00, 2.50, 5.00, and 7.00-to-1. The preferred loading of the Pt is in the range of 0.25 wt % to 5.0 wt %, with weight percentages of 0.10% and 0.05% between, such as 0.35%, 0.45%, 0.75%, 1.10%, 1.15%, 2.00%, 2.50%, 3.0%, and 4.0%.

Preferably, the APR catalyst and the deoxygenation catalyst are of the same atomic formulation. The catalysts may also be of different formulations. The catalysts may also be a single catalyst with both APR and deoxygenation functionality provided by the combination of the above described APR materials and deoxygenation materials. In such event, the preferred atomic ratio of the APR catalyst to the deoxygenation catalyst is in the range of 5:1 to 1:5, such as, without limitation, 4.5:1, 4.0:1, 3.5:1, 3.0:1, 2.5:1, 2.0:1, 1.5:1, 1:1, 1:1.5, 1:2.0, 1:2.5, 1:3.0, 1:3.5, 1:4.0, 1:4.5, and any amounts between.

Similar to the deoxygenation reactions, the temperature and pressure conditions are preferably selected to maintain at least a portion of the feedstock in the liquid phase at the reactor inlet. The reforming temperature and pressure conditions may also be selected to more favorably produce the desired products in the vapor-phase or in a mixed phase having both a liquid and vapor phase. In general, the APR reaction should be conducted at a temperature where the thermodynamics are favorable. For instance, the minimum pressure required to maintain a portion of the feedstock in the liquid phase will vary with the reaction temperature. As temperatures increase, higher pressures will generally be required to maintain the feedstock in the liquid phase. Any pressure above that required to maintain the feedstock in the liquid phase (i.e., vapor-phase) is also a suitable operating pressure. For vapor phase reactions, the reaction should be conducted at a reforming temperature where the vapor pressure of the oxygenated hydrocarbon compound is at least about 0.1 atm (and preferably a good deal higher), and the thermodynamics of the reaction are favorable. The temperature will vary depending upon the specific oxygenated hydrocarbon compound used, but is generally in the range of from about 100° C. to 450° C., or from about 100° C. to 300° C., for reactions taking place in the vapor phase. For liquid phase reactions, the reforming temperature may be from about 80° C. to 400° C., and the reforming pressure from about 72 psig to 1300 psig.

In one embodiment, the reforming temperature is between about 100° C. and 400° C., or between about 120° C. and 300° C., or between about 200° C. and 280° C., or between about 150° C. and 270° C. The reforming pressure is preferably between about 72 and 1300 psig, or between about 72 and 1200 psig, or between about 145 and 1200 psig, or between about 200 and 725 psig, or between about 365 and 700 psig, or between about 600 and 650 psig.

In embodiments where the APR catalyst and the deoxygenation catalyst are combined into a single catalyst, or the reactions are conducted simultaneously in a single reactor, the reforming temperature and deoxygenation temperature may be in the range of about 100° C. to 325° C., or about 120° C. to 300° C., or about 200° C. to 280° C., and the reforming pressure and deoxygenation pressure may be in the range of about 200 psig to 1500 psig, or about 200 psig to 1200 psig, or about 200 psig to 725 psig.

A condensed liquid phase method may also be performed using a modifier that increases the activity and/or stability of the APR catalyst system. It is preferred that the water and the oxygenated hydrocarbon are reacted at a suitable pH of from about 1.0 to 10.0, or at a pH of from about 4.0 to 10.0, including pH value increments of 0.1 and 0.05 between. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of acidic compounds may also provide increased selectivity to the desired reaction products in the hydrogenation reactions described below. It is preferred that the water-soluble acid is selected from the group consisting of nitrate, phosphate, sulfate, chloride salts, and mixtures thereof. If an acidic modifier is used, it is preferred that it be present in an amount sufficient to lower the pH of the aqueous feed stream to a value between about pH 1.0 and about pH 4.0. Lowering the pH of a feed stream in this manner may increase the proportion of oxygenates in the final reaction products.

In general, the reaction should be conducted under conditions where the residence time of the feedstock solution over the APR catalyst is appropriate to generate an amount of APR hydrogen sufficient to react with a second portion of the feedstock solution over the deoxygenation catalyst to provide the desired oxygenates. For example, the WHSV for the reaction may be at least about 0.1 gram of oxygenated hydrocarbon per gram of APR catalyst, and preferably between about 1.0 to 40.0 grams of oxygenated hydrocarbon per gram of APR catalyst, and more preferably between about 0.5 to 8.0 grams of oxygenated hydrocarbon per gram of APR catalyst. In terms of scaled-up production, after start-up, the APR reactor system should be process controlled so that the reactions proceed at steady-state equilibrium.

Biomass Processing Solvent with $C_{4+}$ Compounds

The biomass processing solvent or solvent mixture may also include $C_{4+}$ compounds derived from the further processing of the oxygenates. In such applications, oxygenates are further converted into $C_{4+}$ compounds by condensation in the presence of a condensation catalyst. The condensation catalyst will generally be a catalyst capable of forming longer chain compounds by linking two oxygen containing species through a new carbon-carbon bond, and converting the resulting compound to a hydrocarbon, alcohol or ketone, such as an acid catalyst, basic catalyst or a multi-functional catalyst having both acid and base functionality. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

The condensation catalyst may be self-supporting (i.e., the catalyst does not need another material to serve as a support), or may require a separate support suitable for suspending the catalyst in the reactant stream. One particularly beneficial support is silica, especially silica having a high surface area (greater than 100 square meters per gram), obtained by sol-gel synthesis, precipitation or fuming. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 450° C.

In certain applications, the condensation reaction is performed using acidic catalysts. The acid catalysts may include, without limitation, aluminosilicates (zeolites), silica-alumina phosphates (SAPO), aluminum phosphates (ALPO), amorphous silica alumina, zirconia, sulfated zirconia, tungstated zirconia, tungsten carbide, molybdenum carbide, titania, acidic alumina, phosphated alumina, phosphated silica, sulfated carbons, phosphated carbons, acidic resins, heteropolyacids, inorganic acids, and combinations thereof. In one embodiment, the catalyst may also include a modifier, such as Ce, Y, Sc, La, P, B, Bi, Li, Na, K, Rb, Cs, Mg, Ca, Sr, Ba, and combinations thereof. The catalyst may also be modified by the addition of a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide metal functionality, and/or sulfides and oxide of Ti, Zr, V, Nb, Ta, Mo, Cr, W, Mn, Re, Al, Ga, In, Fe, Co, Ir, Ni, Si, Cu, Zn, Sn, Cd, P, and combinations thereof. Gallium has also been found to be particularly useful as a promoter for the present process. The acid catalyst may be homogenous, self-supporting or adhered to any one of the supports further described below, including supports containing carbon, silica, alumina, zirconia, titania, vanadia, ceria, nitride, boron nitride, heteropolyacids, alloys and mixtures thereof. Ga, In, Zn, Fe, Mo, Ag, Au, Ni, P, Sc, Y, Ta, and lanthanides may also be exchanged onto zeolites to provide a zeolite catalyst having activity. The term "zeolite" as used herein refers not only to microporous crystalline aluminosilicate but also for microporous crystalline metal-containing aluminosilicate structures, such as galloaluminosilicates and gallosilicates. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. Nos. 5,019,663 and 7,022,888, also incorporated herein by reference.

As described in U.S. Pat. No. 7,022,888, the acid catalyst may be a bifunctional pentasil zeolite catalyst including at least one metallic element from the group of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, or a modifier from the group of Ga, In, Zn, Fe, Mo, Au, Ag, Y, Sc, Ni, P, Ta, lanthanides, and combinations thereof. The zeolite preferably has a strong acidic and dehydrogenation sites, and may be used with reactant streams containing and an oxygenated hydrocarbon at a temperature of below 500° C. The bifunctional pentasil zeolite may have ZSM-5, ZSM-8 or ZSM-11 type crystal structure consisting of a large number of 5-membered oxygen-rings, i.e., pentasil rings. The zeolite with ZSM-5 type structure is a particularly preferred catalyst. The bifunctional pentasil zeolite catalyst is preferably Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. The bifunctional ZSM-5 type pentasil zeolite may contain tetrahedral aluminum and/or gallium present in the zeolite framework or lattice and octahedral gallium or indium. The octahedral sites are preferably not present in the zeolite framework but are present in the zeolite channels in a close vicinity of the zeolitic protonic acid sites, which are attributed to the presence of tetrahedral aluminum and gallium in the zeolite. The tetrahedral or framework Al and/or Ga is believed to be responsible for the acid function of zeolite and octahedral or non-framework Ga and/or In is believed to be responsible for the dehydrogenation function of the zeolite.

In one embodiment, the condensation catalyst may be a H-galloaluminosilicate of ZSM-5 type bifunctional pentasil zeolite having framework (tetrahedral) Si/Al and Si/Ga mole ratio of about 10-100 and 15-150, respectively, and non-framework (octahedral) Ga of about 0.5-5.0 wt. %. When these pentasil H-galloaluminosilicate zeolites are used as a condensation catalyst, the density of strong acid sites can be controlled by the framework Al/Si mole ratio:

the higher the Al/Si ratio, the higher the density of strong acid sites. The highly dispersed non-framework gallium oxide species can be obtained by the degalliation of the zeolite by its pre-treatment with $H_2$ and steam. The zeolite containing strong acid sites with high density and also highly dispersed non-framework gallium oxide species in close proximity of the zeolite acid site is preferred. The catalyst may optionally contain any binder such as alumina, silica or clay material. The catalyst can be used in the form of pellets, extrudates and particles of different shapes and sizes.

The acidic catalysts may include one or more zeolite structures comprising cage-like structures of silica-alumina. Zeolites are crystalline microporous materials with well-defined pore structure. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Alternatively, solid acid catalysts such as alumina modified with phosphates, chloride, silica, and other acidic oxides could be used in practicing the present invention. Also, either sulfated zirconia or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. Acidity may also be added to activated carbon by the addition of either sulfates or phosphates.

The condensation reactions result in the production of $C_{4+}$ alkanes, $C_{4+}$ alkenes, $C_{5+}$ cycloalkanes, $C_{5+}$ cycloalkenes, aryls, fused aryls, $C_{4+}$ alcohols, $C_{4+}$ ketones, and mixtures thereof. The $C_{4+}$ alkanes and $C_{4+}$ alkenes have from 4 to 30 carbon atoms ($C_{4-30}$ alkanes and $C_{4-30}$ alkenes) and may be branched or straight chained alkanes or alkenes. The $C_{4+}$ alkanes and $C_{4+}$ alkenes may also include fractions of $C_{4-9}$, $C_{7-14}$, $C_{12-24}$ alkanes and alkenes, respectively, with the $C_{4-9}$ fraction directed to gasoline, the $C_{7-14}$ fraction directed to jet fuels, and the $C_{12-24}$ fraction directed to diesel fuel and other industrial applications. Examples of various $C_{4+}$ alkanes and $C_{4+}$ alkenes include, without limitation, butane, butane, pentane, pentene, 2-methylbutane, hexane, hexane, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecane, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{1+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, and isomers thereof.

Biomass Deconstruction

In the deconstruction process, the biomass slurry is combined with the biomass processing solvent described above and reacted with hydrogen over a deconstruction catalyst to form a biomass hydrolysate. Preferably the biomass slurry comprises 10-50% of the feedstock. The biomass slurry may include any type of biomass, including but not limited to chopped or ground solids, microcrystalline or cotton cellulose, wood or non-wood lignocelluloses, recycle fibers such as newspaper and paperboard, forest and agricultural waste residues, including sawdust, bagasse, and corn stover, and energy crops, such as *miscanthus*, switch grass, sorghum and others. The biomass processing solvent contains a wide range of oxygenates as described above.

The specific products produced will depend on various factors including the composition of the slurry, reaction temperature, reaction pressure, water concentration, hydrogen concentration, the reactivity of the catalyst, and the flow rate of the slurry as it affects the space velocity (the mass/volume of reactant per unit of catalyst per unit of time), gas hourly space velocity (GHSV), and weight hourly space velocity. The deconstruction process can be either batch or continuous. In one embodiment, the deconstruction process is a continuous process using one or more continuous stirred-tank reactors in parallel or in series. In another embodiment, the deconstruction step and the deoxygenation step are conducted in a single reactor.

The deconstruction temperature will generally be greater than 80° C., or 120° C., or 150° C., or 180° C., or 200° C., or 250° C., and less than 350° C., or 325° C., or 300° C., or 280° C., or 260° C. In one embodiment, the deconstruction temperature is between about 80° C. and 350° C., or between about 150° C. and 350° C., or between about 150° C. and 300° C., or between about 200° C. and 260° C., or between about 250° C. and 300° C.

The deconstruction pressure is generally greater than 100 psi, or 250 psi, or 300 psi, or 625 psi, or 900 psi, or 1000 psi, or 1200 psi, and less than 2000 psi, or 1500 psi, or 1200 psi. In one embodiment, the deconstruction temperature is between about 100 psi and 2000 psi, or between about 300 psi and 1500 psi, or between about 1000 psi and 1500 psi. Preferably, the slurry contacts the deconstruction catalyst for between approximately 5 minutes and 2 hours.

In one embodiment, the deconstruction step is performed in the same reactor as the step of catalytically reacting the aqueous feedstock solution with $H_2$ in the presence of a deoxygenation catalyst. In this embodiment, the deconstruction temperature and deoxygenation temperature may be in the range of about 100° C. to 325° C., about 120° C. to 300°

C., or about 200° C. to 280° C., and the deconstruction pressure and deoxygenation pressure may be in the range of about 200 psig to 1500 psig, about 200 psig to 1200 psig, or about 600 psig to 1800 psig.

In general, the reaction should be conducted under conditions where the residence time of the slurry over the catalyst is appropriate to generate the desired products. For example, the WHSV for the reaction may be at least about 0.1 gram of biomass per gram of catalyst per hour, and more preferably the WHSV is about 0.1 to 40.0 g/g hr, including a WHSV of about 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.83, 0.85, 0.85, 1.71, 1.72, 1.73, etc.).

The present invention is able to effectively convert the biomass components to lower molecular weight oxygenated hydrocarbons due to the combination of the processing solvent, the presence of hydrogen in the system, and the unique nature of the deconstruction catalyst. It is believed, that both the processing solvent and the hydrogen facilitate the reaction and conversion process by immediately reacting with the various reaction intermediates and the deconstruction catalyst to produce products that are more stable and less subject to degradation.

The hydrogen used in the deconstruction reaction may be APR $H_2$ or a combination of APR $H_2$, external $H_2$ or recycled $H_2$, or just simply external $H_2$ or recycled $H_2$. In general, the amount of $H_2$ in the deconstruction reactor should maintain the reaction pressure within the system at the desired levels, or increase the molar ratio of hydrogen to carbon and/or oxygen in order to enhance the production yield of certain reaction product types.

The deconstruction process may also include the introduction of supplemental materials to the slurry to assist with the biomass deconstruction or the further conversion of the oxygenated compounds to products more suited for bioreforming processes. Supplemental materials may include dopants, such as acetone, gluconic acid, acetic acid, $H_2SO_4$ and $H_3PO_4$.

The deconstruction process converts the lignin, cellulose and hemicellulose in the liquid and solid phase to an organic complex including carbohydrates, starches, polysaccharides, disaccharides, monosaccharides, sugars, sugar alcohols, alditols, monooxygenates, organic acids, phenols, and cresols. In certain applications, the biomass product stream undergoes one or more separation steps to separate the catalyst (if any), extractives and unreacted biomass from the biomass hydrolysate. The biomass hydrolysate may also require further processing to separate aqueous phase products from organic phase products, such as lignin-based hydrocarbons that are not suitable for bioreforming processes. The biomass hydrolysate may also be dewatered or further purified prior to being introduced into the bioreforming process. Such dewatering and purification processes are known in the art and can include simulated moving bed technology, distillation, filtration, etc.

After separating the impurities, the product stream, suitable for use in bioreforming processes, includes carbohydrates, starches, polysaccharides, disaccharides, monosaccharides, sugars, sugar alcohols, alditols, organic acids, phenols, cresols. The product stream includes smaller oxygenates, such as alcohols, ketones, cyclic ethers, esters, carboxylic acids, aldehydes, diols and other polyols, that may be further converted to $C_{4+}$ hydrocarbons, such as $C_{4+}$ alkanes, $C_{4+}$ alkenes, and aromatic compounds, including benzene, toluene, xylene, using a bioreforming process.

As for the unreacted solids, the deconstruction catalyst can be recycled for re-use in upstream processes. The lignin, ash and other extractives can be purged from the system and used in other processes. For example, the lignin can be burned to provide process heat, while the proteinaceous material can be used for animal feed or as other products.

Recycling of Biomass Processing Solvent

As shown above, the bioreforming process produces a complex mixture of organic compounds. In one embodiment, as illustrated in FIGS. 1 and 2, after completing a bioreforming process such as APR and/or HDO, various process streams can be separated and recycled for use as the biomass processing solvent or directed to further processing for conversion to liquid fuels and chemicals.

In one embodiment, the products from the APR/HDO processes can be separated based on the thermodynamic properties (e.g., boiling point) of the oxygenates using standard fractionation techniques. In such application, the more volatile compounds are separated from a bottom stream containing heavier and less volatile compounds. This heavy bottom stream includes some of the components listed in Table 1 above. The heavy bottom stream can be divided such that some of the heavy bottom stream is recycled into the bioreforming process to undergo further processing, with the remainder of the heavy bottom stream recycled to mix with the biomass slurry prior to the deconstruction process. The organic compounds in the heavy bottom stream help dissolve and crack lignin, which improves lignin removal from the biomass slurry.

In another embodiment of the present invention, an effluent stream can be separated from the bioreforming product stream. This effluent stream includes the organic phase components listed in Table 1, as well as some of the aqueous phase components listed in Table 1. The effluent stream can be recycled to mix with the biomass slurry prior to the deconstruction process. The residual organic acids in the effluent stream can improve biomass deconstruction.

In certain embodiments, the biomass deconstruction and the bioreforming process may be conducted simultaneously in a single reactor. In such embodiments, the deconstruction catalyst and the deoxygenation catalyst may be the same catalyst, or combined into a mixture or arranged in a stacked configuration to promote biomass deconstruction followed by bioreforming. An example of one reactor may include a slurry reactor wherein the biomass is introduced in a first end with a recycle stream that includes both unreacted or underreacted biomass and biomass processing solvent collected from a later heavy bottom stream. The combination of the deconstruction catalyst and the biomass processing solvent promotes biomass deconstruction, which in turn provides oxygenated hydrocarbons for conversion into oxygenates by the deoxygenation catalyst in the reactor. A portion of the oxygenates, in turn, may be either maintained in the reactor, recycled for use as a biomass processing solvent and/or further processed to provide liquid fuels and chemicals.

The biomass deconstruction process described herein efficiently utilizes the available components in lignocellulosic biomass by hydrolyzing the lignin, cellulose and hemicellulose to provide water-soluble oxygenated hydrocarbons for further use in bioreforming processes. The biomass deconstruction process reduces biomass deconstruction costs by avoiding the need to purchase expensive deconstruction solvents and by avoiding solvent recovery and clean-up costs by recycling solvent from intermediates produced in bioreforming processes. The biomass deconstruction process also provides a bioreforming stream by solubilizing lignin, cellulose and hemicellulose components into useable carbohydrates, starches, monosaccharides, disaccharides, polysaccharides, sugars, sugar alcohols, alditols, polyols and mixtures thereof.

EXAMPLE 1

Deconstruction of bagasse was conducted using bioreforming organic phase products as a processing solvent, hydrogen and a Ru:Rh/Darco 200 deconstruction catalyst containing 2.5% ruthenium and 2.5% rhodium. The solvent was composed of 70 wt % water miscible bioreforming organic components and 30 wt % water. A biomass slurry having a biomass concentration of 10 wt % sugarcane bagasse in solvent was reacted over a 90 minute heating period and 30 minute retention period at a temperature of 300° C. and 1200 psi $H_2$. A second and third biomass slurry was reacted without the solvent over the same period at 1200 psi $H_2$ and a temperature of 260° C. and 300° C., respectively.

Figure 3:
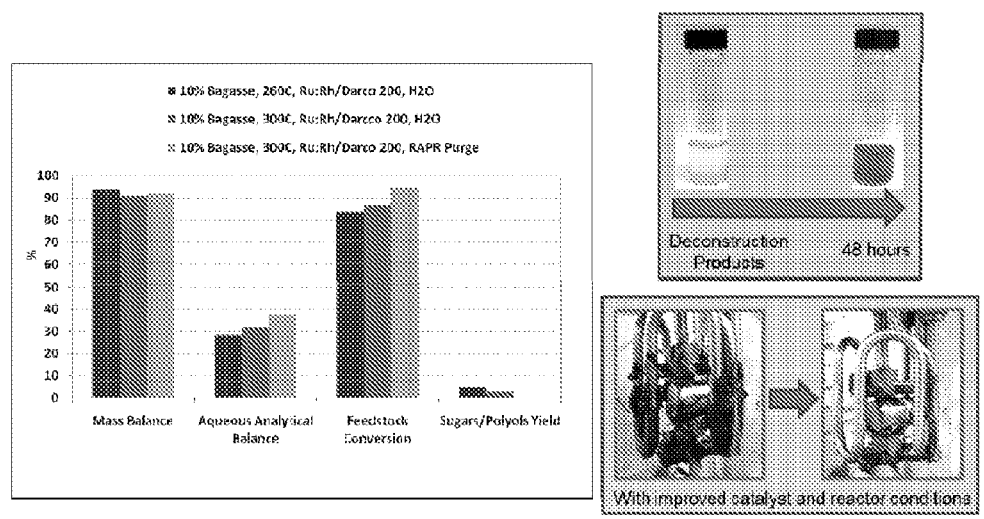
FIG. 3 illustrates the results of organo-catalytic biomass deconstruction using a biomass processing stream from a bioreforming process as an organic solvent.

FIG. 3 shows the experimental results including the yield, aqueous product, and a picture of the reactor following the organo-catalytic deconstruction process. Use of the organic solvent significantly improves biomass deconstruction (from 85% to 95%) and the thick gel that exists in the water medium is solubilized. The removal of the insoluble material significantly improves catalyst lifetime.

EXAMPLE 2

Figure 4:
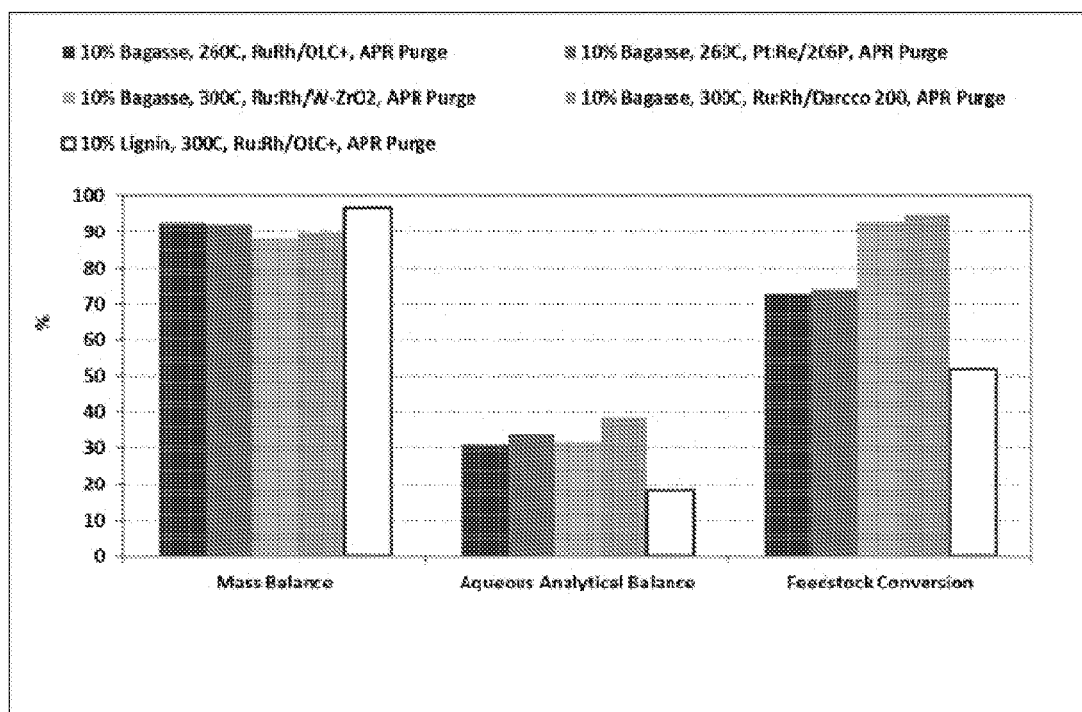
FIG. 4 illustrates the results of organo-catalytic biomass deconstruction using a biomass processing stream from a bioreforming process as an organic solvent and various deconstruction catalysts.

Deconstruction of bagasse and lignin was conducted using bioreforming organic phase products as a processing solvent, hydrogen and various catalysts as depicted in FIG. 4. The solvent was composed of 70 wt % water miscible bioreforming organic components and 30 wt % water. Each biomass slurry had a biomass concentration of 10 wt % biomass (sugarcane bagasse or lignin) in solvent. The biomass slurry was reacted over a 90 minute heating period and 30 minute retention period at a temperature of 300° C. or 260° C. and 1200 psi $H_2$. All catalysts contained metal contents of 2.5 wt % of each metal.

EXAMPLE 3

Figure 5:
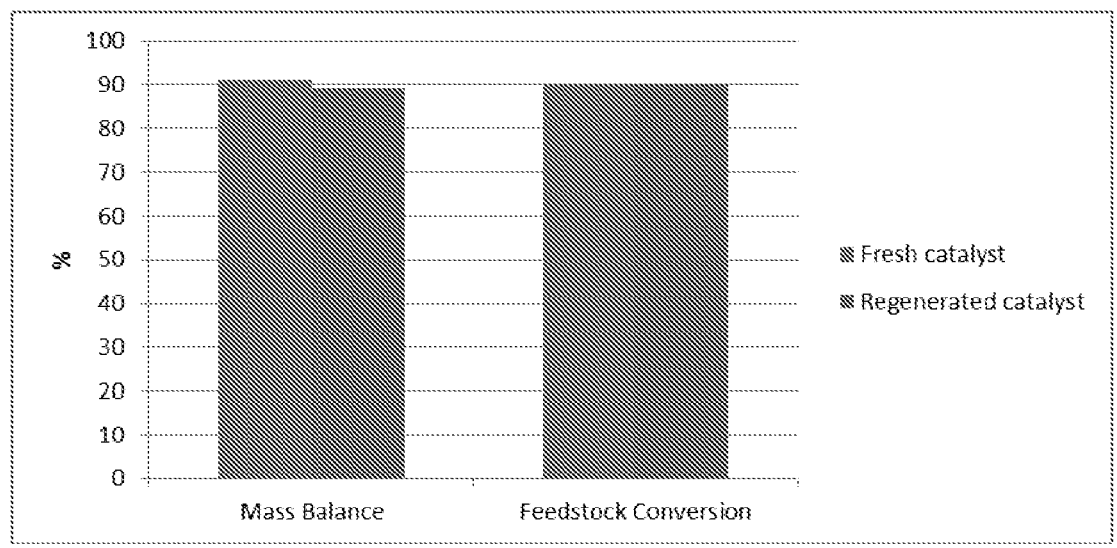
FIG. 5 illustrates the results of organo-catalytic biomass deconstruction using a biomass processing stream from a bioreforming process as an organic solvent and a Pd:Ag/W—$ZrO_2$ deconstruction catalyst.
Figure 6:
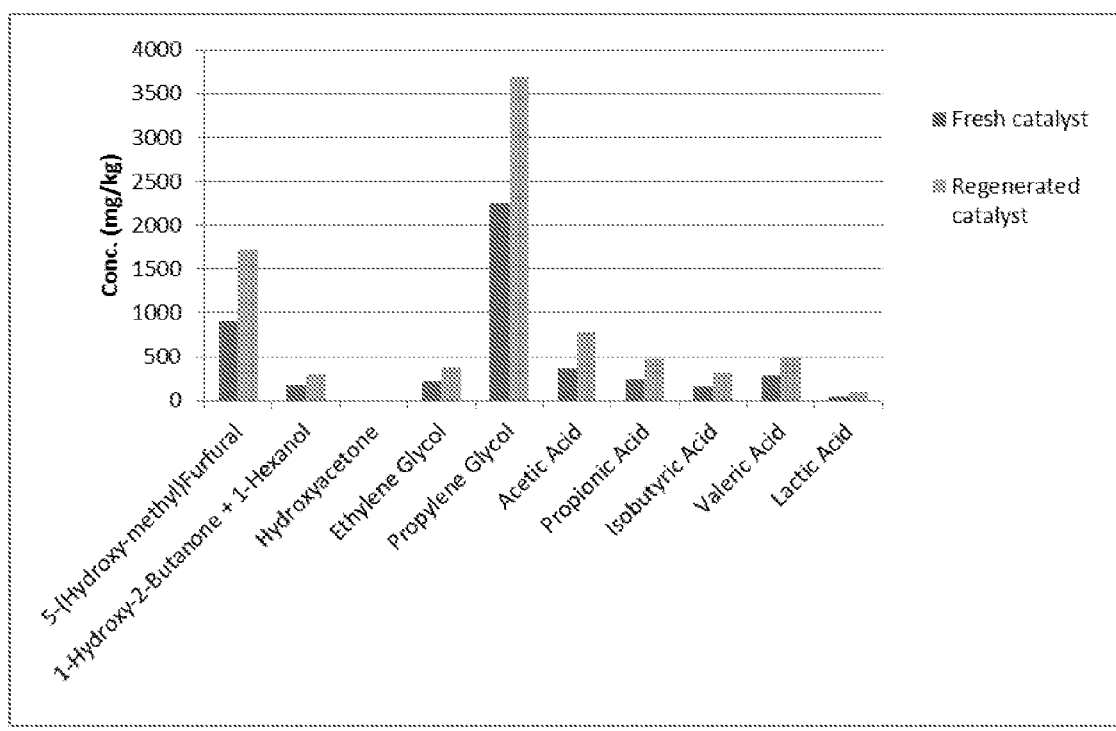
FIG. 6 illustrates the product selectivity of organo-catalytic biomass deconstruction using a biomass processing stream from a bioreforming process as an organic solvent and a Pd:Ag/W—$ZrO_2$ deconstruction catalyst.
Figure 7:
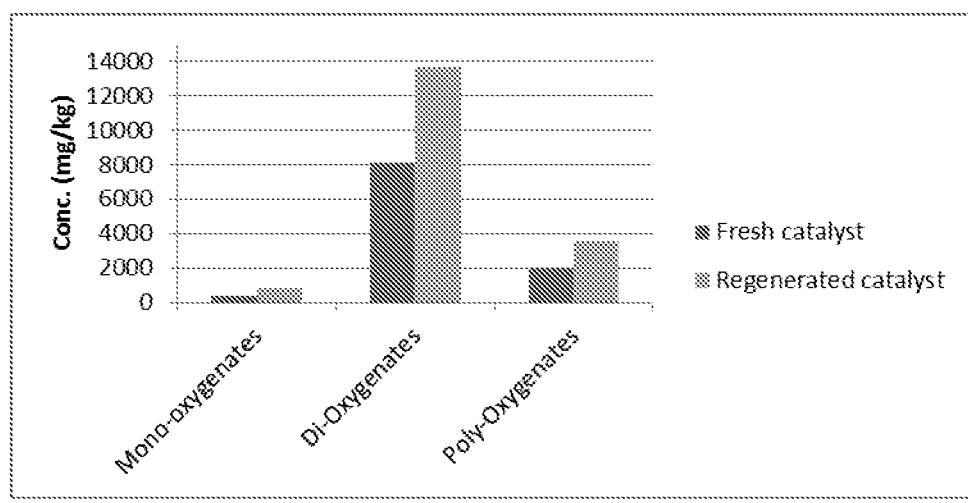
FIG. 7 illustrates the level of oxygenation of the products of organo-catalytic biomass deconstruction using a biomass processing stream from a bioreforming process as an organic solvent and a fresh or regenerated Pd:Ag/W—$ZrO_2$ deconstruction catalyst.
Figure 8:
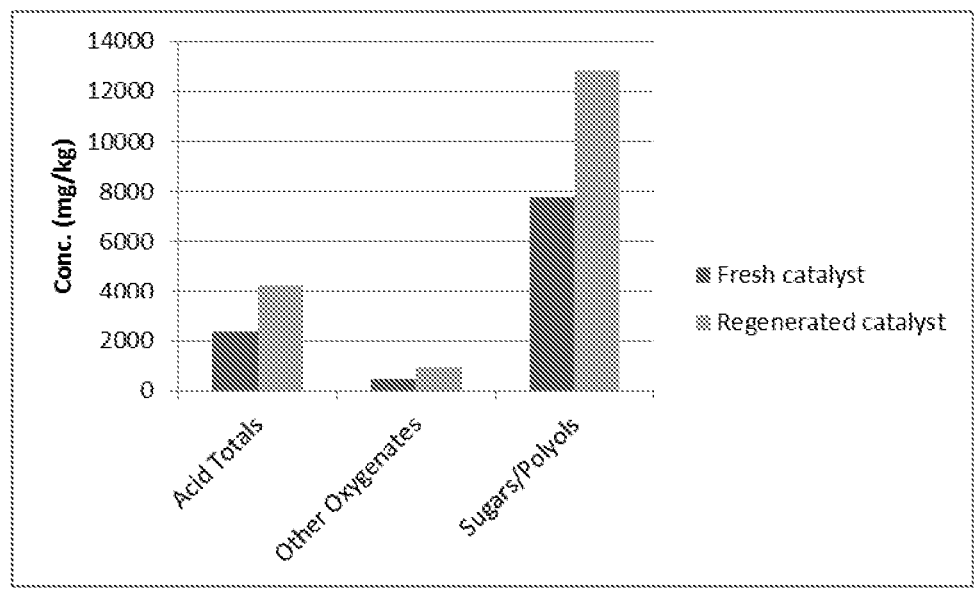
FIG. 8 illustrates the product yields of organo-catalytic biomass deconstruction using a biomass processing stream from a bioreforming process as an organic solvent and a fresh or regenerated Pd:Ag/W—$ZrO_2$ deconstruction catalyst.

Deconstruction of corn stover was conducted using concentrated bioforming aqueous phase reforming products as a solvent, hydrogen and a Pd:Ag/W—$ZrO_2$ deconstruction catalyst containing 2% Pd and Ag. Biomass slurry having a concentration of 10 wt % corn stover in solvent was reacted over a 90 minute heating period at a temperature of 280° C. and 1000 psi $H_2$. The product of this reaction was then reused as the solvent for two subsequent deconstruction trials that followed the same experimental procedures. FIGS. 5 through 8 show the conversion results with both fresh and regenerated catalyst. FIG. 5 indicates that the amount of feedstock converted was the same when using both a fresh and a regenerated catalyst. FIGS. 6-8 show increased product concentrations when a regenerated catalyst was used.

The invention claimed is:

1. A method of making a biomass hydrolysate, the method comprising:
   A. catalytically reacting water and a water-soluble $C_{2+}O_{1+}$ oxygenated hydrocarbon in a liquid or vapor phase with $H_2$ in the presence of a deoxygenation catalyst at a deoxygenation temperature and deoxygenation pressure to produce a biomass processing solvent comprising a $C_{2+}O_{1-3}$ hydrocarbon in a reaction stream; and
   B. reacting the biomass processing solvent with a solid biomass component, hydrogen and a deconstruction catalyst at a deconstruction temperature and a deconstruction pressure to produce a biomass hydrolysate comprising at least one member selected from the group consisting of a water-soluble lignocellulose derivative, a water-soluble cellulose derivative, a water-soluble hemicellulose derivative, a carbohydrate, a starch, a monosaccharide, a disaccharide, a polysaccharide, a sugar, a sugar alcohol, an alditol and a polyol,
   C. recycling the biomass hydrolysate into the reactants of step B.

2. The method of claim 1, wherein the biomass processing solvent comprises a member selected from the group consisting of an alcohol, ketone, aldehyde, cyclic ether, ester, diol, triol, hydroxy carboxylic acid, carboxylic acid, and a mixture thereof.

3. The method of claim 1, wherein the deconstruction catalyst comprises an acidic resin or a basic resin.

4. The method of claim 3, wherein the deconstruction catalyst further comprises a member selected from the group consisting of Fe, Co, Ni, Cu, Ru, Rh, Pd, Pt, Re, Mo, W, an alloy thereof, and a combination thereof.

5. The method of claim 1, wherein the deconstruction catalyst comprises a support and a member adhered to the support, wherein the member is selected from the group consisting of Cu, Fe, Ru, Ir, Co, Rh, Pt, Pd, Ni, W, Mo, an alloy thereof, and a combination thereof.

6. The method of claim 5, wherein the deconstruction catalyst further comprises a member selected from the group consisting of Cu, Mn, Cr, Mo, B, W, V, Nb, Ta, Ti, Zr, Y, La, Sc, Zn, Cd, Ag, Au, Sn, Ge, P, Al, Ga, In, Tl, an alloy thereof, and a combination thereof.

7. The method of claim 1, wherein the oxygenated hydrocarbon is selected from the group consisting of a starch, a carbohydrate, a polysaccharide, a disaccharide, a monosaccharide, a sugar, a sugar alcohol, a alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, and a polyol.

8. A method of making a biomass hydrolysate, the method comprising:
   A. catalytically reacting water and a water-soluble $C_{2+}O_{1+}$ oxygenated hydrocarbon in a liquid or vapor phase with $H_2$ in the presence of a deoxygenation catalyst at a deoxygenation temperature and deoxygenation pressure to produce an oxygenate comprising a $C_{2+}O_{1-3}$ hydrocarbon in a reaction stream;
   B. catalytically reacting in the liquid or vapor phase the oxygenate in the presence of a condensation catalyst at a condensation temperature and condensation pressure to produce a biomass processing solvent comprising one or more $C_{4+}$ compounds; and
   C. reacting the biomass processing solvent with a solid biomass component, hydrogen and a deconstruction catalyst at a deconstruction temperature and a deconstruction pressure to produce a biomass hydrolysate comprising at least one member selected from the group consisting of a water-soluble lignocellulose derivative, a water-soluble cellulose derivative, a water-soluble hemicellulose derivative, a carbohydrate, a starch, a monosaccharide, a disaccharide, a polysaccharide, a sugar, a sugar alcohol, an alditol, and a polyol, D. recycling the biomass hydrolysate into the reactants of step C.

9. The method of claim 8, wherein the biomass processing solvent comprises a member selected from the group consisting of an alkane, alkene and an aromatic.

10. The method of claim 9, wherein the biomass processing solvent comprises a member selected from the group consisting of benzene, toluene and xylene.

11. The method of claim 8, wherein the deconstruction catalyst comprises an acidic resin or a basic resin.

12. The method of claim 11, wherein the deconstruction catalyst further comprises a member selected from the group consisting of Fe, Co, Ni, Cu, Ru, Rh, Pd, Pt, Re, Mo, W, an alloy thereof, and a combination thereof.

13. The method of claim 8, wherein the deconstruction catalyst comprises a support and a member adhered to the support selected from the group consisting of Cu, Fe, Ru, Ir, Co, Rh, Pt, Pd, Ni, W, Mo, an alloy thereof, and a combination thereof.

14. The method of claim 13, wherein the deconstruction catalyst further comprises a member selected from the group consisting of Cu, Mn, Cr, Mo, B, W, V, Nb, Ta, Ti, Zr, Y, La, Sc, Zn, Cd, Ag, Au, Sn, Ge, P, Al, Ga, In, Tl, an alloy thereof, and a combination thereof.

15. The method of claim 8, wherein $C_{2+}O_{1+}$ hydrocarbon is selected from the group consisting of a starch, a carbohydrate, a polysaccharide, a disaccharide, a monosaccharide, a sugar, a sugar alcohol, a alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, and a polyol.

16. The method of claim 8, wherein the condensation catalyst comprises a member selected from the group consisting of a carbide, a nitride, zirconia, alumina, silica, an aluminosilicate, a phosphate, a zeolite, a titanium oxide, a zinc oxide, a vanadium oxide, a lanthanum oxide, a yttrium oxide, a scandium oxide, a magnesium oxide, a cerium oxide, a barium oxide, a calcium oxide, a hydroxide, a heteropolyacid, an inorganic acid, an acid modified resin, a base modified resin, and combinations thereof.

* * * * *

UNITED STATES PATENT AND TRADEMARK OFFICE
CERTIFICATE OF CORRECTION

PATENT NO. : 9,518,305 B2
APPLICATION NO. : 14/968361
DATED : December 13, 2016
INVENTOR(S) : Ming Qiao, Randy D. Cortright and Elizabeth Woods It is certified that error appears in the above-identified patent and that said Letters Patent is hereby corrected as shown below:

In the Specification

Column 14, Line 58 - "VIM" should be --VIIB--

Signed and Sealed this
Twenty-first Day of March, 2017

Michelle K. Lee
*Director of the United States Patent and Trademark Office*